United States Patent
Fuentes Garcia et al.

(10) Patent No.: US 10,788,481 B2
(45) Date of Patent: Sep. 29, 2020

(54) ONE STEP PHAGOCYTOSIS-CELL ACTIVATION-CELL DEATH ASSAY

(71) Applicants: UNIVERSIDAD DE SALAMANCA, Salamanca (ES); IMMUNOSTEP S.L., Salamanca (ES)

(72) Inventors: Manuel Fuentes Garcia, Salamanca (ES); Paula Diez Garcia, Salamanca (ES); Cristina Isabel Gonçalves Grunho Tedosio, Salamanca (ES); Alberto Orfao de Matos, Salamanca (ES); Ricardo Jara Acevedo, Salamanca (ES)

(73) Assignees: UNIVERSIDAD DE SALAMANCA, Salamanca (ES); IMMUNOSTEP S.L., Salamanca (ES)

( * ) Notice: Subject to any disclaimer, the term of this patent is extended or adjusted under 35 U.S.C. 154(b) by 113 days.

(21) Appl. No.: 15/641,743

(22) Filed: Jul. 5, 2017

(65) Prior Publication Data

US 2018/0011083 A1 Jan. 11, 2018

(30) Foreign Application Priority Data

Jul. 5, 2016 (EP) .................................... 16382317

(51) Int. Cl.
*C07K 16/28* (2006.01)
*G01N 33/50* (2006.01)
*G01N 33/569* (2006.01)
*A61B 5/00* (2006.01)
*G01N 33/58* (2006.01)

(52) U.S. Cl.
CPC ....... *G01N 33/5047* (2013.01); *A61B 5/4848* (2013.01); *A61B 5/4869* (2013.01); *C07K 16/28* (2013.01); *C07K 16/2809* (2013.01); *C07K 16/2812* (2013.01); *G01N 33/505* (2013.01); *G01N 33/5014* (2013.01); *G01N 33/5055* (2013.01); *G01N 33/5091* (2013.01); *G01N 33/5094* (2013.01); *G01N 33/56972* (2013.01); *G01N 33/582* (2013.01)

(58) Field of Classification Search
CPC ........... G01N 33/5047; G01N 33/5014; G01N 33/5091; G01N 33/5094; G01N 33/56972; G01N 33/582; G01N 33/505; G01N 33/5055; C07K 16/28; C07K 16/2812; C07K 16/2809; A61B 5/4848; A61B 5/4869
See application file for complete search history.

(56) References Cited

U.S. PATENT DOCUMENTS 7,351,546 B2 * 4/2008 Willmann .......... G01N 33/5002
435/287.2
2016/0003840 A1 * 1/2016 Perez ................. G01N 33/5008
506/9

FOREIGN PATENT DOCUMENTS

WO WO 2008/010843 A2 1/2008
WO WO 2012/164008 A1 12/2012

OTHER PUBLICATIONS

Hanley et al The Influences of Cell Type and ZnO Nanoparticle Size in Immune Cell Cytotoxicity and Cytokine Function. Nanoscale Res Lett 4: 1409-1420 (2009).*
Cory Hanley et al: "The Influences of Cell Type and ZnO Nanoparticle Size on Immune Cell Cytotoxicity and Cytokine Induction", Nanoscale Research Letters, vol. 26, No. 12, Sep. 16, 2009 (Sep. 16, 2009), pp. 1113-1420.
Ellen B. Cook et al: "Regulation of the 11-16 Receptor for TNF[alpha], TNFRI, in Human Conjunctival Epithelial Cells", Investigative Opthalmology & Visual Science, vol. 49, No. 9, Sep. 1, 2808 (Sep. 1, 2008), pp. 3992-3998.
Extended European Search Report in corresponding European Application No. 16382317.2, dated Nov. 3, 2016.

* cited by examiner

*Primary Examiner* — Gailene Gabel
(74) *Attorney, Agent, or Firm* — Leason Ellis LLP

(57) ABSTRACT

The invention relates to methods to evaluate in one single assay the biocompatibility of materials based on the simultaneous determination of the phagocytosis, cell activation and cell death produced by said materials, preferably, in peripheral blood or other human cells and proximal fluids. The invention also relates to a kit to perform the method of the invention.

10 Claims, 4 Drawing Sheets

ONE STEP PHAGOCYTOSIS-CELL ACTIVATION-CELL DEATH ASSAY

The invention relates to methods to evaluate in one single assay the biocompatibility of materials based on the simultaneous determination of the phagocytosis, cell activation and cell death produced by said materials, preferably, in peripheral blood or other human cells and proximal fluids. The invention also relates to a kit to perform the method of the invention.

BACKGROUND ART

The nanoscience revolution that sprouted throughout the 1990s is becoming part of our daily life in the form of cosmetics, food packaging, drug delivery systems, therapeutics, or biosensors, among others. Indeed, it has been estimated that the production of nanomaterials would increase in 2020 by 25 times what it is today covering a wide range of applications in numerous fields (e.g. cosmetics, household appliances, semiconductor devices, energy sources, food color additives, surface coatings, biological sensors and probes, drug carriers, implants and medical imaging).

Due to the nanoscale dimensions of nanoparticles (NPs), they can be easily uptaken by the cells, not only by themselves but also by bypassing natural mechanical barriers after protein-coating. Different biological mechanisms can facilitate the entrance of NPs depending on their physical and chemical properties (i.e. phagocytosis, micropinocytosis, or endocytosis).

In order to understand the exact cellular influences of NPs, a thorough characterization of individual NPs is necessary. They can get into the human body through several ways (e.g. skin penetration, inhalation or injection) and due to their small size and diffusion abilities, they have the potential to interact with cells and organs. In addition to the involuntary exposure of NPs by means of contacting nanomaterials-based products, there are cases where NPs could interact with the human body for biomedical purposes.

In case of usage of NPs for targeted drug delivery, NPs are required to traverse the cell membranes and interact with specific components. Hence, the success rate of drug delivery is mainly based on the NP biocompatibility. Several researches have shown that different physical-chemical properties of NPs result in different cellular uptake. Currently, it has been described that several factors play a critical role in toxicity, such as (i) size and surface (key point for liposomes, silicon microparticles, quantum dots, polymeric and gold NPs); (ii) concentration, crystallinity and mechanical strength; and (iii) chemical attributes (e.g. hydrophilic polymer functionalization—with polyethylene glycol or poly carboxy betaine—at the surface of NPs enhances the systemic circulation).

The discovery of enhanced permeation and retention (EPR) effect and its combination with hydrophilic polymers are related to the accumulation of NP-based carrier systems in tumor tissues followed by the release of the drug either in the proximity of the tissue. However, EPR effect is commonly inconsistent due to the heterogeneity associated with the tumor tissue. For this reason, novel nanomedicines are being designed and developed in order to target only a particular cell, tissue, and organ by linking an affinity reagent to the NP which is targeting a specific biomolecule differentially expressed at the tissue or cells of interest.

Since several concerns have been raised about poor systemic circulation, enhanced clearance by the mononuclear phagocytic system has been shown to improve the cellular uptake and efficacy of the NP payload in comparison with passively targeted counterparts. Bearing in mind that most of the targets present intracellular location, the characterization of endocytosis pathways is a key point when designing nanomaterials with efficient intracellular trafficking, subcellular targeting, and nanomedicines with ideal features (high-phagocytosis, low-toxicity, and low immune response).

Related to the characterization of nanomaterials and nanomedicines and the features mentioned above, studies regarding these points are still highly limited, although some approaches have been accomplished to determine the phagocytosis, toxicity and immune response of nanomaterials.

1.1. Phagocytosis Assays

Conventional immune phenotyping or microscopy approaches (i.e. confocal, optical, fluorescence, transmission electron microscopy (TEM) or scanning electron microscopy (SEM)) can be employed to evaluate the cell uptake of nanomaterials. Additional, cell staining could be required to better visualize the internalization of nanomaterials.

1.2. Toxicity Assays

The biological characterization of nanomaterials that will be in contact with food or humans is a key to guaranteeing their safety. The most conventional assays to evaluate cytotoxicity are based on measuring the cell activity of different components (e.g. mitochondrial activity for MTT assay, the release of the enzyme lactate dehydrogenase (LDH) for LDH leakage assay or the reducing power of cells for resazurin-based assays). All these approaches are tedious, time-consuming and highly-dependent of a highly-qualified technician; and habitually do not allow high-density assays because are not easy to automate. Additionally, the cytotoxicity assays can be supplemented by other studies, such as trypan blue (TB) and propidium iodide (PI) protocols.

1.3. Immunological Studies

NPs play an important role in medicine area and their properties can be used to improve traditional treatments and diagnostic agents. Although there are many biocompatibility studies about size, shape, charge, solubility and surface modification of NPs, the interactions between NPs and the immune system and the derived immune response are still not well understood.

According to the literature, NPs can activate and/or suppress the immune response and the compatibility with this system is determined by their surface chemistries. Therefore, NPs could be designed to avoid immune toxicity and reach desirable immunomodulation.

Preclinical data shows that NPs are not more immune toxic than conventional drugs, so NPs employed like drug carriers could provide advantages in the nanomedicine field. For instance, NPs can release the drug in a specific tissue in order to not alter safe tissues and they may keep drugs away from blood cells. Moreover, NPs can also decrease drug immune toxicity by raising their solubility. However, NPs are generally picked up by phagocytic cells of the immune system (macrophages, monocytes, neutrophils, dendritic cells, mast cells) which could promote immune stimulation or autoimmune disorders due to the generated immune stimulation or immunosuppression.

To characterize the immune stimulation or immune suppression is required the quantitative identification of cells of the immune system and cytokines levels. Commonly, enzyme-linked immunosorbent assay (ELISA) is used for quantitative detection of cytokines or immunoglobulins.

Additionally, cytometric bead arrays (CBA) can be employed to simultaneously detect and evaluate the cytokine profile production.

To date, despite the immense progress on the evaluation of biocompatibility of nano-/micromaterials and nano-/micromedicines, it is still necessary a novel approach which could provide in one single step an optimal understanding of the interaction between nano-/micromaterials and the animal body.

For this purpose, the main goal of this invention is the design and development of a one single multiparametric assay which allows the quantitative evaluation of toxicity, phagocytosis capacity and activation of the immune system in a very fast manner.

DESCRIPTION OF THE INVENTION

The present invention is based on the inventors' studies regarding materials, in particular, nanomaterials, and their use in the delivery of drugs within the animal body. The authors of the present invention have discovered that it is possible to asses in one single step the cytotoxicity, immune modulation and phagocytosis of a material by means of flow cytometry based on the response of the cell populations to said material. This method allows the skilled person in the art to assess in a simple way the biocompatibility of a material and its potential use as a delivery carrier in the animal body.

As is shown herein in the appended examples, the inventors isolated the peripheral blood mononuclear (PBMN) cells, incubated with latex beads, and put them into contact with different monoclonal antibodies directed against specific proteins present in different cell populations (CD45, CD4, CD3 and CD14), an apoptosis marker (Annexin V), and an immune modulation marker (TNFalpha). Next, the cells were passed through a flow cytometer, identifying the different population cells (monocytes, T-CD4$^+$ lymphocytes, T-CD4$^-$ lymphocytes), the viable cells (Annexin$^-$ cells), the immune stimulated cells (TNFalpha$^+$ cells) and the phagocytic cells (FITC$^+$ cells). Finally, in view of cells state, it was concluded that latex beads (analyzed nanomaterial) were compatible with the animal body (Examples 2 and 3).

Thus, in one aspect, the present invention relates to a method for the simultaneous evaluation of cytotoxicity, immune modulation and phagocytosis induction of a material, hereinafter "method of the invention", comprising:
a) incubating a biological sample with the material for obtaining stimulated cell populations;
b) incubating the stimulated cell populations of step a) with
 fluorochrome-labeled antibodies specific for monocytes markers, T-CD4$^+$ lymphocytes markers, T-CD4$^-$ lymphocytes markers and markers of molecules involved in immune modulation,
 an inhibitor of protein secretion, and
 viability cell markers,
  wherein each marker is detected with a different fluorochrome,
c) passing the cell population resulting from step b) through a flow cytometer and measuring the different fluorescent emissions in a single measurement; and
e) assessing the degree of viable cells, activated cells and phagocytic cells in each cellular population by determining the amount of fluorescent related signal associated with every individual cell and with every individual immune modulation molecule/marker used.

The present invention relates to a method for the simultaneous evaluation of cytotoxicity, immune modulation and phagocytosis induction of a material.

In the present invention, the term "simultaneous" means that only one assay is needed in order to know the cytotoxicity, the immune modulation and the phagocytosis induction of a material. As will be explained bellow, the only assay needed is performed by flow cytometry assay.

In the present invention, the term "cytotoxicity" means that something (e.g. the material) is toxic to the cell. Treating cells with the cytotoxic compound can result in a variety of cell fates. The cells may undergo necrosis, in which they lose membrane integrity and die rapidly as a result of cell lysis. The cells can stop actively growing and dividing (a decrease in cell viability), or the cells can activate a genetic program of controlled cell death (apoptosis). As the skilled person knows, compounds which have cytotoxic effects often compromise cell membrane integrity.

In the present invention, the term "immune modulation" means that something (e.g. the material) is capable of inducing a response of the immune system when it is administered to the animal body. This response comprises, among others, the cell secretion of cytokines.

In the present invention, the term "phagocytosis induction" means that something (e.g. the material) induces a process by which a cell engulfs a solid particle to form an internal vesicle known as a phagosome. In an organism's immune system, phagocytosis is the major mechanism used to remove pathogens and cell debris.

The material to be tested by the method of the invention is a natural, incidental or manufactured material containing particles, in an unbound state or as an aggregate or as an agglomerate and where one or more of its external dimensions comprises a size ranging from 0.001 µm to 1000 µm. Thus, the material comprises both nano- and micromaterial. The term "nanomaterial" means that the material size ranges from 1 nm to 100 nm (0.001 µm to 0.1 µm). The term "micromaterial" means that the material size ranges from above 0.101 µm to 1000 µm. Examples of micromaterials include, but without limited to, pearls, beads and microparticles. Examples of nanomaterials include, but without limited to, nanoperls, nanobeads and nanoparticles. Likewise, the material may be, but not limited to, polymers, such as latex and PET, dextranes, hydrogels, liposomes, polymersomes, chitosans and starches. Additionally, the material may show any shape, such as tubes, wires, pearls, beads, particles, etc. as the skilled person understand, any of these materials can be use as a drug delivered carrier and/or may be in combination with small molecules such as drugs, DNA and/or RNA probes, peptides, etc.

In a particular embodiment, the material is a nanomaterial or a micromaterial, preferably, the nanomaterial or micromaterial is a particle, more preferably, a bead or a pearl.

In a first step [step a)], the method of the invention comprises incubating a biological sample with the nano-/micromaterial for obtaining a stimulated cell population.

Any biological sample can be used for putting into practice the method of the invention. The term "biological sample" refers to any material coming from a subject and comprising cells. The cell population is typically present in a sample. The sample is preferably a fluid sample.

The sample typically comprises a body fluid of the patient. The sample may be lymph, cerebrospinal fluid (CSF) or amniotic fluid but is preferably peripheral blood, blood, plasma or serum, pleural effusion, bone marrow, lymph node, lymph fluid, synovial fluid, a single cell suspension prepared from a solid tissue and cell lines. The sample may be from bone marrow. Typically, the sample is human in origin, but alternatively, it may be from another mammal animal such as from commercially farmed animals such as horses, cattle, sheep or pigs or may alternatively be pets such as cats or dogs.

The sample is typically processed prior to being assayed, for example by centrifugation or by passage through a membrane that filters out unwanted molecules or cells, such as red blood cells. The sample may be measured immediately upon being taken. The sample may also be either freshly harvested from the subject or stored prior to assay. If cryopreserved, the sample may be typically stored below −196° C.

It will be understood that other samples may also be used by the method presented herein, such as cell cultures, tissues or solid tumors. In a particular embodiment, the biological sample is selected from the group consisting of peripheral blood, ascetic fluid, pleural effusion, cerebrospinal fluid (CSF), bone marrow, lymph node, lymph fluid, synovial fluid, a single cell suspension prepared from a solid tissue and cell lines.

Methodologies for the isolation of peripheral blood, PBMN cells, blood and CSF are well known in the art. Typically, blood is drawn from a vein (venipuncture) and bone marrow is aspirated from the posterior iliac crest. Specimens are typically collected in the presence of an anticoagulant such as, for example, ethylenediaminetetraacetic acid (EDTA) or heparin.

Red blood cells in blood or bone marrow samples are, generally, removed by a lysis procedure or by density gradient centrifugation, by standard methods.

Once the biological sample is isolated from the subject, the sample is put into contact with the material (nano-/micromaterial) in order to stimulate the cell populations present in the sample. Optionally, the sample may be additionally put into contact with adjuvants agents for enhancing the stimulation of the cell populations, either at the same time that the material or before/after the contact of the sample with the material.

As the skilled person knows, when a foreign object is detected by the cells, these cells release cytokines which recruit lymphocytes (CD4+ and CD4-) and monocytes and trigger an immune response. Accordingly, the cells of the biological sample are stimulated, and the type, amount and stage of said cells (i.e. of the different population cells) will depend on the strength of the immune response.

In the context of the present invention, "stimulated cell populations" means a set of cell populations whose phenotype has changed as a consequence of an external stimulus.

Next, once the cell populations have been stimulated by the material, the method of the invention comprises [step b)] incubating the stimulated cell populations with
fluorochrome-labeled antibodies specific for monocytes markers, T-CD4+ lymphocytes markers, T-CD4− lymphocytes markers and markers of molecules involved in immune modulation,
an inhibitor of protein secretion, and
viability cell markers,
wherein each marker is detected with a different fluorochrome.

Any fluorochrome can be used for labeling the antibodies. A fluorochrome is a fluorescent chemical compound that can re-emit light upon light excitation. Thus, the fluorochrome may also be referred to as a fluorescent marker, a fluorescent stain or a fluorescent dye. Such a fluorochrome may, for example, be a fluorescent marker with a particular fluorescent emission signature when subjected to incident light.

Multiple different markers may be used for different components in the sample that is being prepared for flow cytometry evaluation. For example, a first marker in the form of a fluorescent dye having an affinity for a specific marker (e.g., CD13, CD14, CD45, etc.) may have a particular fluorescent emission wavelength range and a second marker in the form of a second fluorescent dye with an affinity for another maker may have a different fluorescent emission wavelength range. Examples of fluorescent markers include, but not limited to, fluorescein isothiocyanate (FITC), phycoerythrin (PE), peridinin chlorophyll protein (PerCP), allophycocyanin (APC), Alexa fluor 488, Alexa 647, Alexa 710, Alexa fluor 405, cyanin 5 (Cy5), cyanin 5.5 (Cy5.5), pacific blue (PacB), horizon violet 450 (HV450), pacific orange (PacO), brilliant violet (BV), HV500, 00515, Krome Orange, CF Blue, or conjugates thereof coupled to PE, APC or PerCP, and any combination thereof. Thus, in a particular embodiment, the fluorochromes are selected from the group consisting of fluorescein isothiocyanate (FITC), phycoerythrin (PE), peridinin chlorophyll protein (PerCP), allophycocyanin (APC), Alexa fluor 488, Alexa 647, Alexa 710, Alexa fluor 405, cyanin 5 (Cy5), Cyanin 5.5 (Cy5.5), pacific blue (PacB), horizon V450 (HV450), pacific orange (PacO), brilliant violet (BV), Horizon V500, 00515, Krome Orange, CF Blue, quantum dots or conjugates thereof coupled to PE, APC or PerCP, and any combination thereof. Methods for labeling antibodies with the cited markers are widely known in the state of the art further to be commercially available.

Antibodies that are capable of specifically binding to the various cells surface markers are known in the art. An antibody "specifically binds" to a cell surface marker when it binds with preferential or high affinity to that marker but does not substantially bind, does not bind or binds with only low affinity to other cell surface markers or other proteins. For instance, an antibody "specifically binds" to CD13 when it binds with preferential or high affinity to CD13 but does not substantially bind, does not bind or binds with only low affinity to other cell surface markers or proteins, such as CD90, CD105, CD14, CD19, CD34, and CD45.

An antibody binds with preferential or high affinity if it binds with a Kd of $1\times10^7$M or less, more preferably $5\times10^8$M or less, more preferably $1\times10^8$M or less or more preferably $5\times10^9$M or less. A portion binds with low affinity if it binds with a Kd of $1\times10^5$M or more, more preferably $1\times10^5$M or more, more preferably $1\times10^4$M or more, more preferably $1\times10^3$M or more, even more preferably $1\times10^2$M or more. A variety of protocols for competitive binding or immunoradiometric assays to determine the specific binding capability of compounds, such as antibodies or antibody constructs are well known in the art.

The antibody may be, for example, a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')2 or Fv fragment. Fluorescent labels suitable for use in the method of the invention were discussed above.

In the context of the present invention, the labeled antibodies specifically bind to monocytes markers, T-CD4+ lymphocytes markers, T-CD4− lymphocytes markers, viability/apoptosis cell markers and markers of molecules involved in immune modulation.

Examples of monocytes, T-CD4+ lymphocytes, and T-CD4− lymphocytes markers include, but without limiting to, CD14, CD4, CD3, CD45, HLA-DR, CD3, CD19, CD56, CD14, CD33, CD123, CD16, CD15, CD64, and combinations thereof. In a particular embodiment, the monocytes, T-CD4+ lymphocytes and T-CD4− lymphocytes markers are selected from CD14, CD4, CD3, CD45 and any combination thereof.

In the present invention, "markers of molecules involved in the immune modulation" refers to those molecules which are secreted or recruited by a cell as a response to an external stimulus. An example of markers of molecules involved in immune modulation includes, but without limiting to, Tumor Necrosis Factor alpha (TNFalpha), Interferon gamma (IFNγ) (all interferons), Interleukin 6 (IL6), Interleukin 12 (IL12), Tumor Necrosis Factor beta (TNFβ), Interleukin 2 (IL2), Interleukin 8 (IL8), Interleukin 10 (IL10), Interleukin 13 (IL13), and Interleukin 16 (IL16). In a particular, embodiment, the markers of molecules involved in immune modulation are selected from TNFalpha, IFNγ (all interferons), IL6, IL12, TNFβ, IL2, IL8, IL10, IL13, IL16 and any combination thereof.

Examples of viability cell markers include, but without limiting to, Annexin V, Propidium Iodide (PI); 4',6-Diamidino-2-phenylindole dihydrochloride (DAPI); 7-amino-actinomycin D (7-AAD); DRAQ7™ (Deep Red Anthraquinone 7 or Propietary derivative of 1,5-bis{[2-(di-methylamino)ethyl] amino}-4,8-dihydroxyanthracene-9,10-dione); DRAQ5™ (Deep Red Anthraquinone 5 or Propietary derivative of 1,5-bis{([2-(di-methylamino)ethyl] amino}-4,8-dihydroxyanthracene-9,10-dione); TO-PRO-3® (Thermo Fisher); SYTOX® DNA-binding dyes (Thermo Fisher). In a particular embodiment, the viability cell markers are selected from Annexin V, Propidium Iodide; 4',6-Diamidino-2-phenylindole dihydrochloride; 7-amino-actinomycin D; DRAQ7™; DRAQ5™; TO-PRO-3® and SYTOX® DNA-binding dyes.

The antibodies used in the FACS method may typically be titrated for use in the method as discussed below. The reason for titrating antibodies for flow cytometry is to allow optimal separation between positive and negative signals without unnecessarily wasting antibody, thus reducing background noise and the overall cost of the method. Too high antibody concentrations in the staining volume can also lead to non-specific antibody binding. Titration is, therefore, good practice, not only to increase the specificity of the assay but also to reduce reagent consumption and thus cost (ICSH ICCS, 2013, Flow Cytometry Guidelines). The goal of the titration is to identify the antibody concentration that results in the highest stain index. This is routine in the art.

In order to put into practice step b) of the method of the invention, each marker has to be detected with a different fluorochrome. Doing this, each cell population which expresses a specific marker can be identified by a flow cytometer using the appropriate gates, analyzing the effect of the material over the cell populations of the biological sample.

Additionally, the step b) of the method requires the presence of a protein secretion inhibitor. In the context of the present invention, a protein secretion inhibitor is a compound capable of preventing a protein from being secreted by the cell.

As the skilled person understands, this inhibition allows the detection of the secreted protein. Thus, the protein secretion inhibitor to be chosen for carried out the method of the invention depends on the protein which is going to be detected. Protein secretion inhibitors are widely known from the state of the art. In a particular embodiment, the protein secretion inhibitors are metalloprotease inhibitors. Examples of metalloprotease inhibitors include, without limiting to, TAPI-2, TAPI-0, batimastat, NNGH, galardin and RO32-7315. In a more particular embodiment, the metalloprotease inhibitor is TAPI-2. By using metalloprotease inhibitor, in particular, the TAPI-2 compound, the secretion of TNFalpha (and molecules whose show the same mechanism of secretion) is inhibited and its detection is possible.

Another compound following within the scope of protein secretion inhibitors is Brefeldin A. As the skilled person in the art knows, Brefeldin A is an inhibitor of intracellular protein transport. Incubation of cells in culture with Brefeldin A leads to blockade of protein transport to the Golgi complex (GC) and accumulation of proteins in the endoplasmic reticulum (ER). Addition of Brefeldin A during the last hours of in vitro activation of cells results in enhanced detection of intracellular cytokines. Brefeldin A is effective for enhanced detection of a majority of mouse and human intracellular cytokines.

In the next step of the method of the invention [step c)], the cell population resulting from step b) is passed through a flow cytometer and the different fluorescent emissions are measured in a single step.

Flow cytometry is a technique in which microscopic particles are suspended in a stream of fluid, and are measured or quantitated by a laser beam based on chemical or physical characteristics of the particle, such as fluorescence or light scattering. In the present invention, the particles to be analyzed by flow cytometer are cells. Flow cytometers are capable of measuring features of cells which have been labeled with compounds that make them fluoresce. Flow cytometry enables researchers to observe characteristics of a large number of particles.

The detectors used in flow cytometry can obtain information about objects by receiving signals from them, for example, signals in the form of light emanating from an object, whether through emission (e.g. radiation, fluorescence, incandescence, chemiluminescence, bioluminescence, other forms of luminescence, etc.), scattering (e.g. reflection, deflection, diffraction, refraction, etc.), or transmission, and can be sensed by a photodetector. Cells or other particles (e.g. antibodies) may be treated, e.g., stained or tagged with a suitable fluorescent probe or another agent, in such a way that they emit light or absorb light in a predictable fashion when illuminated with measurement light. In flow cytometry, the biochemical selection of a (sub-) population of objects is often performed with fluorescent probes. For example, propidium iodide stains dead cells, while SYTO® 9 stains live cells. Another example is DAPI (4',6-diamidino-2-fenilindol) which is known to stain cell nuclei.

Further embodiments of the present disclosure encompass systems and methods for assessing positivity in multicolor flow cytometry. Exemplary specificity or gating control techniques can be used to evaluate an individual particle signature, for example to determine whether a blood cell is positive or negative for a certain protein expression, such as a marker of a specific cell population (monocytes markers, T-CD4+ lymphocytes markers, T-CD4− lymphocytes markers and markers of molecules involved in immune modulation, etc.). In some cases, these control techniques can be used to position a gate or graphical region relative to acquired data, so as to classify the cells from which the data is obtained. Exemplary control techniques can be used in multicolor procedures following compensation.

In some cases, the emission spectra measured from different fluorescent dyes may overlap, and it may be helpful to compensate the signals obtained by the detectors. For example, a fluorescence compensation technique can be applied during data analysis so as to determine how much interference that Fluorochrome A is having in Channel B (which is assigned to specifically measure Fluorochrome B). As a result, it is possible to obtain the total measured fluorescence at Channel B, and subtract the contribution of Fluorochrome A, so as to determine the fluorescence of Fluorochrome B at Channel B.

Event data can be visually depicted in a variety of ways. For example, a histogram can be used to display a single measurement parameter (e.g. fluorescence) on the horizontal X-axis and the number of events (e.g. cell count) on the vertical Y-axis. In this way, it is possible to determine the number of cells in a sample having certain characteristics. For example, a short peak on the left side of the graph may represent a small group of cells having a dim fluorescence (events within a negative population) and high peak on the right side of the graph may represent a large group of cells having a bright fluorescence (events within a positive population).

As used herein, a "gate" can be used as a boundary to differentiate between a positive population and a negative population. Similarly, a gate can be used as a boundary to define a subpopulation of events. A gate can be set, for example, by delineating a boundary around a subset of events on a data plot such as a dot plot or histogram. A gate can be inclusive so as to select events that fall within a boundary, or exclusive so as to select events that fall outside of the boundary. Accordingly, the number of positive events (on a particular side of the boundary) can refer to the number of cells displaying a physical feature or marker of interest. According to some embodiments of the present invention, gating can be used to distinguish signals corresponding to fluorescent objects from signals corresponding to non-fluorescent objects. Hence, an emitted fluorescence can be associated with a specific label.

Specific gating protocols are available for diagnostic and clinical purposes in the field of the invention. For example, gates can be used in flow cytometry data to selectively visualize certain cells of interest such as white blood cells, while eliminating results from unwanted particles such as dead cells and debris. In some situations, it can be difficult to determine where to place a gate so as to effectively classify an event as either positive or negative. By using an appropriate control, it is possible to help identify the difference between a positive population and a negative population. Embodiments of the present invention can be used in conjunction with multicolor cytometry techniques in general.

Relatedly, the present invention encompasses post-acquisition correction techniques for flow cytometry, such that compensation errors associated with acquired sample results can be minimized. For example, the use of standard compensation approaches in multi-color channel experiments with fixed correction values can tend to either overcompensate or undercompensate the experiment results at a gating border.

After measuring the different fluorescent emissions by flow cytometry, the method of the invention comprises assessing the degree of viable cells, activated cells, and phagocytic cells by determining the amount of fluorescent related signal associated with every individual cell marker and with every individual immune modulation involved molecule marker used.

This step comprises the data analysis by properly choosing the gate (as explained above) for detecting a specific fluorescent emission associated with the marker which will be indicative of the presence/absent of a particular cell population and/or a particular molecule involved in the immune modulation. Flow cytometry analysis data software is widely known in the state of the art and any of them can be used to put into practice the present invention.

In view of the markers used in the method of the invention, the cell populations to be analyzed are monocytes, T-CD4$^+$ lymphocytes, T-CD4$^-$ lymphocytes and, within hemapoptotic cells, positive cells for molecules involved in immune modulation and phagocytic cells.

For example, in a particular embodiment, data analysis was performed in five steps (see Example 2). First, the cells of interest are selected (white blood cells) and cell debris and cell aggregates are excluded, based on the expression of CD45 and light dispersion characteristics (forwards side scatter—FSC—and sideward side scatter—SSC—). Secondly, the monocytes (CD14$^{++}$/CD4$^+$/CD3$^-$/CD45$^+$), the T-CD4$^+$ lymphocytes (CD45$^{++}$/CD3$^+$/CD4$^+$/CD14$^-$), and the T-CD4$^-$ lymphocytes (CD45$^{++}$/CD3$^+$/CD4$^-$/CD14$^-$) were identified and selected. Thirdly, Annexin V-CF™Blue positive cells were selected within each population corresponding to apoptotic cells. Afterwards, non-annexin positive cells (corresponding to viable cells) were used for determining TNFalpha-APC positive cells (for measuring the immune response). The effect of the stimulation in each cell population was assessed on unstimulated samples as a control and TNFalpha production was based on the percentage of positive cells, after subtracting the percentage of cells staining above the threshold for positivity in the negative control. Finally, phagocytic cells were identified selecting positive cells in the FITC channel.

Thus, at the end of this analysis, based on the kind of cell populations detected in the biological sample in response to the material, it is possible to know in a single step the cytotoxicity, immune modulation and phagocytosis induction of said nanomaterial, which will be indicative of the biocompatibility of the material.

Therefore, in another aspect, the invention relates to a method for assessing the biocompatibility of a material comprising:
(a) evaluating the cytotoxicity, immune modulation and phagocytosis of said material by a method according to the method of the invention, and
(b) comparing the results obtained in (a) with a control profile obtained by the same method but without the material,
wherein a lower degree of cytotoxicity, immune activity, and/or phagocytosis than the control profile is indicative that the material is biocompatible.

In the context of the present invention, the term "biocompatible" means the ability of a material to perform with an appropriate host response in a specific application, or to be in contact with a living system without producing an adverse effect.

In a particular embodiment, the material is a nanomaterial or a micromaterial, preferably, the nanomaterial or micromaterial is a particle, more preferably, a bead or a pearl. The terms "material", "nanomaterial" and "micromaterial" has been defined previously in the present description.

In a particular embodiment, the material is a nano-/microparticle with a drug conjugated acting as a carrier for selective and particular delivery in a target tissue or organ.

All the particular embodiments disclosed for the method of the invention are applicable to the present method.

Additionally, the invention relates the kits comprising one or more other reagents or instruments which enable any of the embodiments mentioned above to be carried out. Such reagents or instruments include one or more of the following: suitable buffer(s) (aqueous solutions) and/or other reagents needed for FACS analysis, such as labeled antibodies and apoptosis markers. Reagents may be present in the kit in a dry state such that a fluid sample re-suspends the reagents. The kit may also, optionally, comprise instructions to enable the kit to be used in the method of the invention.

Thus, in another aspect, the present invention relates to a kit comprising
- labeled antibodies specific for monocytes markers, T-CD4$^+$ lymphocytes markers, T-CD4$^-$ lymphocytes markers and markers of molecules involved in immune modulation,
- an inhibitor of protein secretion and
- viability cell markers.

In a particular embodiment of the kit of the invention, the monocytes, T-CD4$^+$ lymphocytes and T-CD4$^-$ lymphocytes markers are selected from CD14, CD4, CD3, CD45 and any combination thereof.

In another particular embodiment, the viability cell markers are selected from Annexin V, Propidium Iodide; 4',6-Diamidino-2-phenylindole dihydrochloride; 7-amino-actinomycin D; DRAQ7; DRAQ5; TO-PRO-3 and SYTOX® DNA-binding dyes.

In another particular embodiment, the markers of molecules involved in immune modulation are selected from TNFalpha, IFNγ, IL6, IL12, TNFβ, IL2, IL8, IL10, IL13, IL16 and any combination thereof.

In another particular embodiment, the fluorochromes are selected from the group consisting of fluorescein isothiocyanate, phycoerythrin, peridinin chlorophyll protein, allophycocyanin, Alexa fluor 488, Alexa 647, Alexa 710, Alexa fluor 405, cyanin 5, cyanin 5.5, pacific blue, horizon V450, pacific orange, brilliant violet, horizon V500, Orange Cytognos (OC) 515, Krome Orange, CF Blue, quantum dots or conjugates thereof coupled to PE, APC or PerCP and any combination thereof.

In another particular embodiment, the inhibitor of protein secretion is a metalloprotease inhibitor, preferably, the metalloprotease inhibitor is TAPI-2.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages, and features of the invention will become apparent to those skilled in the art upon examination of the description or may be learned by practice of the invention. The following examples, drawings, and sequence listing are provided by way of illustration and are not intended to be limiting of the present invention.

EXAMPLES

Example 1—Simultaneous Multiparametric Flow Cytometry Analysis of Viability and Immune Response to Different Stimuli 1.1 Material and Methods Heparin anti-coagulated peripheral blood (PB) samples were obtained from 2 healthy individuals and processed within the first 2 hours after collection for simultaneous analysis of viability and immune response to distinct stimuli (i.e. activation of T lymphocytes and monocytes, measured by the expression of TNFalpha).

1. 2. Sample Preparation

Figure 1:
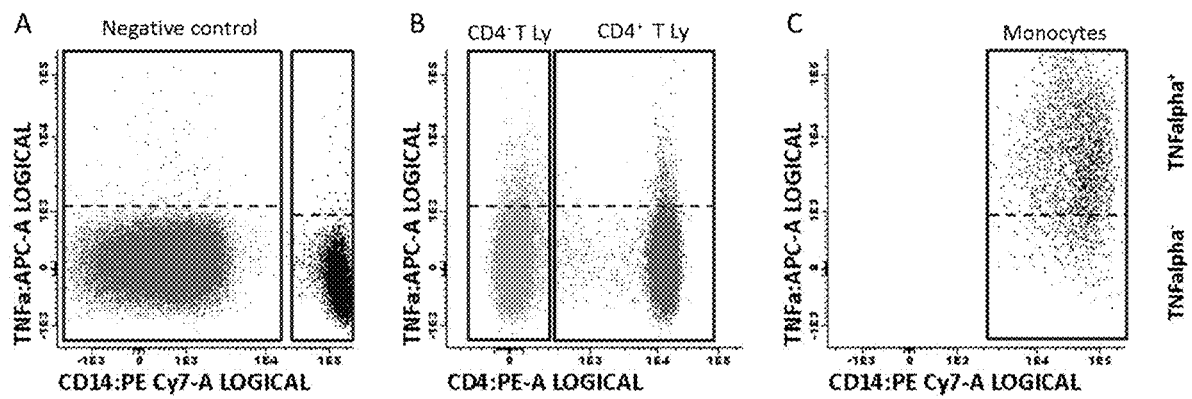
FIG. 1—Precise discrimination of activated cells (showing higher levels of expression of TNFalpha), upon stimulation with LPS plus IFNgamma, can be performed comparing to an unstimulated control used as negative control (Panel A) to set the threshold above which TNFalpha positive cells can be identified. The gating for TNFalpha positive CD4$^+$ and CD4$^-$ T lymphocytes (CD4$^+$ T Ly and CD4$^-$ T Ly, respectively) was performed in a TNFalpha-CD4 dot plot (Panel B). In the case of monocytes, a TNFalpha-CD14 dot plot was employed (Panel C).
Figure 2:
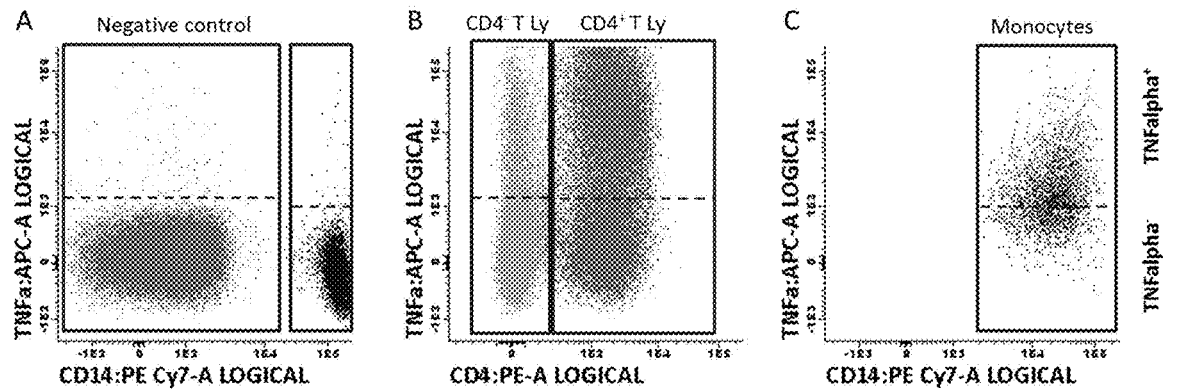
FIG. 2—Precise discrimination of activated cells (showing higher levels of expression of TNFalpha), upon stimulation with PMA plus ionomycin, can be performed comparing to an unstimulated control used as negative control (Panel A) to set the threshold above which TNFalpha positive cells can be identified. The gating for TNFalpha positive CD4$^+$ and CD4$^-$ T lymphocytes (CD4$^+$ T Ly and CD4$^-$ T Ly, respectively) was performed in a TNFalpha-CD4 dot plot (Panel B). In the case of monocytes, a TNFalpha-CD14 dot plot was employed (Panel C).

Peripheral blood mononuclear cells (PBMN cells) were purified by density gradient centrifugation using Biocoll Separating Solution (Biochrom, Germany), according to the manufacturer's protocol. After centrifugation, the PBMN cells interphase was collected and quantified using a Neubauer chamber. The PBMN cell culture was carried out in RPMI-1640 media supplemented with 10% heat-inactivated fetal bovine serum, 1% glutamine, and 1% penicillin/streptomycin and 40 µM TACE inhibitor—TAPI-2—(Sigma-Aldrich, St. Louis/MO, USA) in a 24-well plate (2 cm$^2$ diameter). TAPI-2 was used as secretion blocking agent for detection of membrane-bound TNFalpha. Alternatively, 10 µg/mL of Brefeldin A (Sigma-Aldrich) was used to inhibit cytokine transport from the endoplasmic reticulum to the Golgi apparatus, instead of the TACE inhibitor, as a control condition for TAPI-2. In these control conditions, TNFalpha expression was assessed intracellularly. For stimulation purposes 100 ng/mL lipopolysaccharide (LPS) (Sigma-Aldrich) plus 10 ng/mL IFNgamma (Promega, Madison/WI, USA) (FIG. 1) or 10 ng/mL of phorbol 12-myristate 13 acetate (PMA) (Sigma-Aldrich) plus 0.75 µg/mL of ionomycin (Sigma-Aldrich) (FIG. 2) were added, to stimulate (i.e. induce cytokine secretion) monocytes and T lymphocytes. As a basal activation control, cells were incubated without the different stimuli. The PBMN cells were incubated in darkness at 37° C. in 5% CO$_2$ atmosphere for 4 hours.

After this incubation period, cells from each well were collected in a tube using phosphate buffer saline solution (pH 7.4) (PBS). Adherent cells were detached by gentle scrapping. Then, cells were centrifuged at 400 g for 10 minutes. The supernatant was discarded and the cell pellet was resuspended in 2 mL of PBS. Another centrifugation (400 g, 10 minutes) was performed and cells were finally resuspended in 0.1 mL of PBS solution.

For those conditions incubated with TAPI-2, surface membrane staining was performed to identify the distinct populations of interest and assess the expression of TNFalpha. Therefore, each sample was stained with the following combination of monoclonal antibodies. The specificity of the monoclonal antibodies used, their origins and their fluorochromes were as follows:

CD3 APC-H7 (Clone SK7); T-lymphocyte marker (BD, San Jose/Calif., USA)
CD4 PE (Clone HP2/6); cytotoxic T-lymphocyte marker (ImmunoStep, Salamanca)
CD14 PE-Cy7 (Clone RM052); monocyte marker (BD, San Jose/Calif., USA)
CD45 PerCPCy5.5 (Clones 2D1); pan-leucocyte marker (BD, San Jose/Calif., USA)
TNFalpha APC (Clone MAb11); immune response marker (BD, San Jose/Calif., USA)

The tubes were gently vortexed and incubated in the dark for 15 minutes at room temperature. Immediately after this incubation period, 2 mL of PBS was added to each tube followed by gentle vortex and a centrifugation at 400 g for 5 minutes. The supernatant was discarded and a new washing step with 2 mL of PBS was performed. Afterwards, 0.2 mL of 1× annexin V binding buffer was added followed by the annexin V-CF™Blue apoptosis marker (ImmunoStep, Salamanca/Spain). Cells were incubated for 15 minutes at room temperature and were stored at 4° C. in the darkness until analyzed in the flow cytometer.

For those activation control conditions incubated with Brefeldin A, surface membrane staining was performed with monoclonal antibodies aimed at the identification of populations of interest and an intracellular staining was made for the assessment of TNFalpha production.

The specificity of the monoclonal antibodies used, their origins and their fluorochromes were as follows:

CD3 APC-H7 (Clone SK7); T-lymphocyte marker (BD, San Jose/Calif., USA)
CD4 PE (Clone HP2/6); cytotoxic T-lymphocyte marker (ImmunoStep, Salamanca)
CD14 PE-Cy7 (Clone RM052); monocyte marker (BD, San Jose/Calif., USA)
CD45 PerCPCy5.5 (Clones 2D1); pan-leucocyte marker (Becton Dickinson Biosciences, BD, San Jose/Calif., USA)
TNFalpha APC (Clone MAb11); immune response marker (BD, San Jose/Calif., USA)

For staining procedure, CD3 APC-H7, CD4-PE, CD14 PE Cy7 and CD45 PerCP Cy5.5 monoclonal antibodies were added and the cells were incubated for 15 minutes at room temperature in the darkness. Cells were washed with 2 mL of PBS and centrifuged for 5 minutes at 400 g and the supernatant was discarded. Cells were then fixed with 100 µL of reagent A (fixation solution; Fix&Perm™, An der Grub, Vienna, Austria) and incubated for 15 minutes in the dark at room temperature. After this period, 2 mL of PBS was added and the suspension was centrifuged for 5 minutes at 400 g, and the supernatant was discarded. Cell pellet was resuspended by mixing gently and 100 µL of Reagent B (permeabilizing solution; Fix&Perm™) was added simultaneously with the antibody against the intracellular protein (TNFalpha). The tubes were gently vortexed and incubated in the dark for 15 minutes at room temperature. After this period, cells were washed twice with 2 mL of PBS (5 minutes at 400 g) and cells resuspended in 0.3 mL of PBS for acquisition.

1.3. Data Acquisition and Analysis

Data acquisition was performed on a FACSCanto II flow cytometer (Becton Dickinson Biosciences, BD, San Jose/Calif., USA) using the FACSDiva software (v6.1; BD). For data analysis, the Infinicyt™ software (Cytognos SL, Salamanca, Spain) was used.

Figure 3:
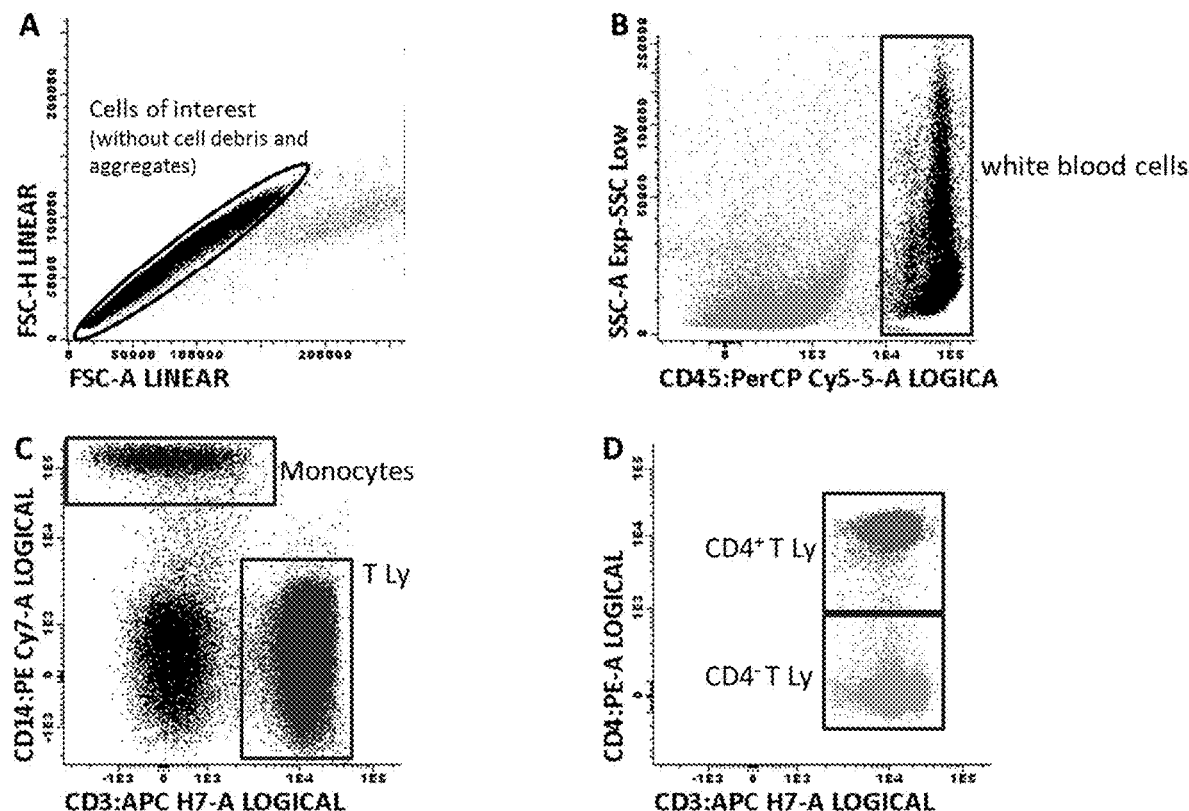
FIG. 3—Populations of interest (monocytes and lymphocytes T) can be detected by accurate flow cytometry gating strategies after staining for expression of CD3, CD4, CD14, and CD45. In the presented staining, first gating on the diagonal of FSC-H and FSC-A is performed (Panel A) to eliminate the cell debris and the cell aggregates followed by gating based on positivity for CD45 (Panel B). Monocytes and T lymphocytes can be accurately identified gating on CD14 expressing cells vs. CD3 expressing cells, respectively (Panel C). The T lymphocytes selected can be further evaluated with the CD4 marker, resulting in two subsets: CD4$^+$ T lymphocytes and CD4$^-$ T lymphocytes (Panel D).
Figure 4:
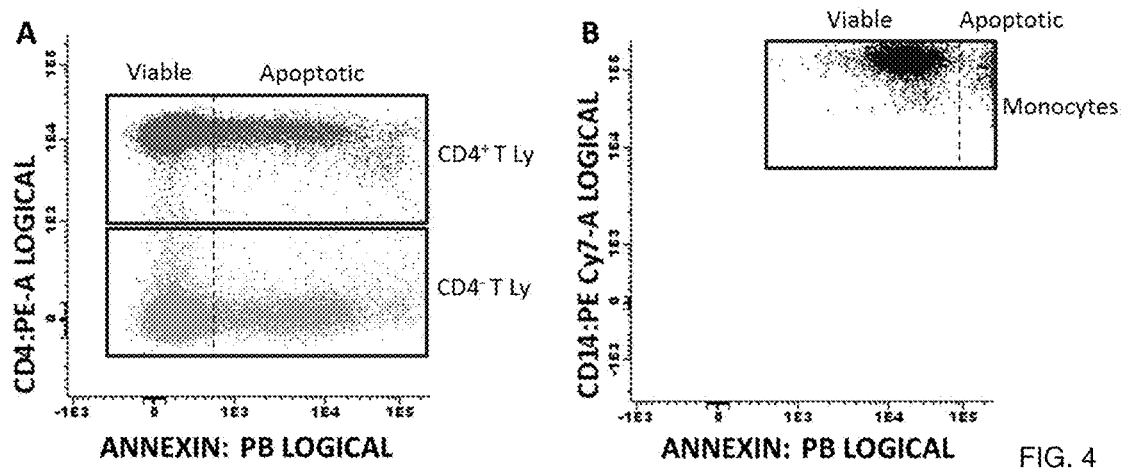
FIG. 4—Results of viability analysis after incubation of PBMN cells with carboxylate-modified polystyrene fluorescent yellow-green latex beads for 4 hours. Staining for annexin V allowed the distinction between apoptotic cells (positivity for annexin) and viable cells (negativity for annexin). The gating for annexin positive CD4$^+$ and CD4$^-$ T lymphocytes (CD4$^+$ T Ly and CD4$^-$ T Ly, respectively) was performed in an annexin-CD4 dot plot (Panel A). In the case of monocytes, an annexin-CD14 dot plot was employed (Panel B).

Data analysis was performed in four steps. First, we selected the cells of interest (white blood cells) and excluded cell debris and cell aggregates, based on the expression of CD45 and light dispersion characteristics (forwards side scatter—FSC—and sideward side scatter—SSC—). Secondly, we identified and selected the monocytes (CD14$^{++}$/CD4$^+$/CD3$^-$/CD45$^+$), the T-CD4$^+$ lymphocytes (CD45$^{++}$/CD3$^+$/CD4$^+$/CD14$^-$), and the T-CD4$^-$ lymphocytes (CD45$^{++}$/CD3$^+$/CD4$^-$/CD14$^-$) (FIG. 3). Thirdly, for those tubes labelled with Annexin V, apoptotic cells were identified within each population as those cells in which Annexin V-CF™Blue signal was detected (FIG. 4). Afterwards, non-annexin positive cells (corresponding to living cells) were used for determining TNFalpha-APC positive cells (for measuring the immune response). Both in the control conditions incubated with TAPI-2 (for plasma membrane detection of TNFalpha) and those conditions incubated with Brefeldin A (for intracellular detection of TNFalpha), the effect of the stimulation in each cell population was assessed on unstimulated samples as a control and TNFalpha production was based on percentage of positive cells, after subtracting the percentage of cells staining above the threshold for positivity in the negative control.

1.4. Results

The usage of PMA plus ionomycin activation stimuli during 4 hours, in presence of TACE-inhibitor, lead to significant apoptosis induction in monocytes, CD4+, and CD4− T cells (89.0±10.9%, 35.4±2.8% and 51.7±1.7% Annexin V positive cells, respectively), compared to the unstimulated controls (13.1±3.7%, 14.9±2.4% and 24.1±6.3%, respectively). This was also observed, in less extent, also for LPS plus IFNgamma stimuli (80.4±14.9%, 15.9±2.0% and 24.6±1.5% Annexin V positive cells, respectively).

Activation of monocytes, CD4+ and CD4− T cells was observed as a result of incubation of PBMN cells with PMA plus ionomycin in presence of TACE inhibitor (62.5±0.5%, 30.1±19.7% and 7.6±1.7% TNFalpha positive cells, respectively), compared to the unstimulated controls (2.5±2.2%, 1.5±1.4%, and 1.9±1.8%, respectively). Conversely, stimulation with LPS and IFNgamma only induced significant activation on monocytes vs. CD4+ and CD4− T cells (81.6±8.7% vs. 1.6±0.8% and 2.2±1.7% TNFalpha positive cells, respectively). A similar pattern was observed for those cases in which inhibition of TNFalpha release was performed using Brefeldin A, with 55.0±11.8%, 66.7±9.5% and 35.0±1.5% TNFalpha positive cells, observed for monocytes, CD4+ and CD4− T cells stimulated with PMA plus ionomycin; 97.9±2.0%, 13.4±12.3% and 14.3±14.7% TNFalpha positive cells, respectively when LPS and IFNgamma were used as stimuli, all compared to the unstimulated control (32.7±22.6%, 13.8±12.8% and 15.7±15.3% TNFalpha positive cells, respectively).

1.5. Conclusion

By one single assay, it is possible the simultaneous characterization of activated lymphocytes and/or monocytes cells against an antigen stimulus; in addition, this assay allows the quantitative discrimination between activated vs non-activated cells; among others cells presented in a complex biological sample (i.e. peripheral blood) by immunophenotypic analysis.

Example 2—Multiparametric Analysis of Phagocytosis, Viability, and Immune Response after Incubation with Fluorescent Beads 2.1. Material and Methods Peripheral blood (PB) was obtained by venous puncture from 2 healthy individuals, placed in lithium heparin tube and processed within the first 2 hours after collection for simultaneous analysis of viability, phagocytosis and immune response to incubation with fluorescent beads.

2.2. Sample Preparation

Peripheral blood mononuclear cells (PBMN cells) were purified by density gradient centrifugation using Biocoll Separating Solution (Biochrom, Germany), according to the manufacturer's protocol. After centrifugation, the PBMC interphase was collected and quantified using a Neubauer chamber.

A total of $0.2 \times 10^6$ PBMN cells were cultured in RPMI-1640 medium supplemented with 10% heat-inactivated fetal bovine serum, 1% glutamine, 1% penicillin/streptomycin and 40 μM TACE inhibitor—TAPI-2—(Sigma-Aldrich, St. Louis/MO, USA) in a 24-well plate (2 cm² diameter). TAPI-2 was used as secretion blocking agent to reveal the levels of TNFalpha. The sample was incubated with $1 \times 10^6$ and $2 \times 10^6$ latex beads (carboxylate-modified polystyrene, 2 μm diameter) labelled with a fluorescent yellow-green fluorochrome (fluorochrome detectable in the FITC channel) (Sigma-Aldrich, St. Louis/MO, USA) for 5 beads/cell and 10 beads/cell conditions, respectively. The wells were incubated in darkness at 37° C. in 5% $CO_2$ atmosphere for 4 hours.

After this incubation period, cells from each well were collected in a tube using phosphate buffer saline solution (PBS) (pH 7.4). (Note: after the incubation period, supernatants can be saved for further analysis by ELISA or CBA approaches, for instance). If necessary, a cell scraper was used to detach the adherent cells. Then, cells were centrifuged at 400 g for 10 minutes. The supernatant was discarded and the cell pellet was resuspended in 2 mL of PBS. Another centrifugation (400 g, 10 min) was performed and cells were finally resuspended in 0.1 mL of PBS solution.

Afterwards, each sample was incubated with five monoclonal antibodies. The specificity of the monoclonal antibodies used, their origins and their fluorochromes were as follows:

CD3 APC-H7 (Clone SK7); T-lymphocyte marker (BD, San Jose/Calif., USA)

CD4 PE (Clone HP2/6); cytotoxic T-lymphocyte marker (ImmunoStep, Salamanca)

CD14 PE-Cy7 (Clone RM052); monocyte marker (BD, San Jose/Calif., USA)

CD45 PerCPCy5.5 (Clones 2D1); pan-leucocyte marker (Becton Dickinson Biosciences, BD, San Jose/Calif., USA)

TNFalpha APC (Clone MAb11); immune response marker (BD, San Jose/Calif., USA)

The tubes were gently vortexed and incubated in the dark for 15 minutes at room temperature. Immediately after this incubation period, 2 mL of PBS was added to each tube followed by gentle vortex. Then, samples were centrifuged at 400 g for 5 minutes. The supernatant was discarded and a new centrifugation step was performed. Afterwards, 0.2 mL of 1× annexin V binding buffer was added followed by the annexin V-CF™Blue apoptosis marker (ImmunoStep, Salamanca/Spain). Cells were incubated for 15 minutes at room temperature and were stored at 4° C. in the darkness until analyzed in the flow cytometer.

Note: samples from Example 1 can be employed as controls for activation of the immune response as well as for cell apoptosis.

2.3. Data Acquisition and Analysis

Data acquisition was performed on a FACSCanto II flow cytometer (Becton Dickinson Biosciences, BD, San Jose/Calif., USA) using the FACSDiva software (v6.1; BD). For data analysis, the Infinicyt™ software (Cytognos SL, Salamanca, Spain) was used.

Figure 5:
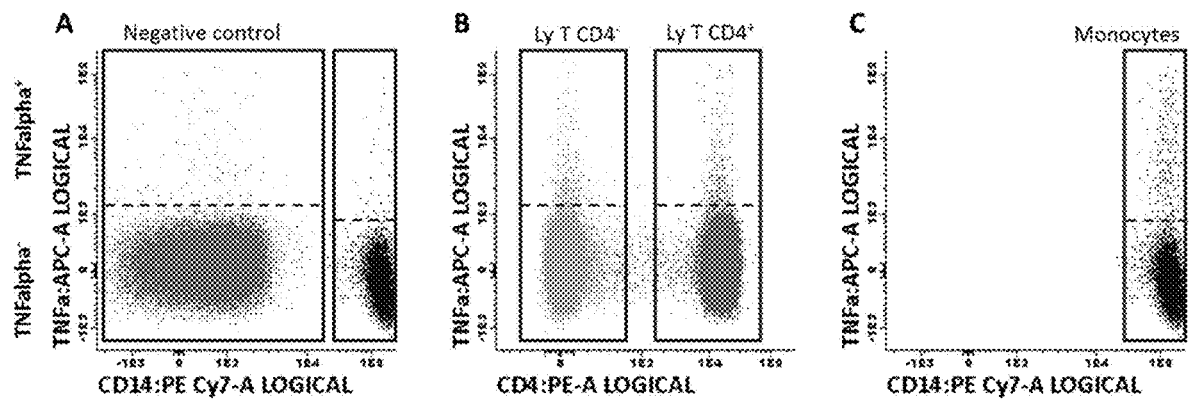
FIG. 5—Results of immune system stimulation analysis after incubation of PBMN cells with carboxylate-modified polystyrene fluorescent yellow-green latex beads for 4 h at a ratio of 10 beads per cell. Staining for TNFalpha allowed the distinction between activated cells (positivity for TNFalpha) and non-activated cells (negativity for TNFalpha). An unstimulated control without beads can be used as a negative control (Panel A) to set the threshold above which TNFalpha positive cells can be identified. The gating for TNFalpha positive CD4$^+$ and CD4$^-$ T lymphocytes (CD4$^+$ T Ly and CD4$^-$ T Ly, respectively) was performed in a TNFalpha-CD4 dot plot (Panel B). In the case of monocytes, a TNFalpha-CD14 dot plot was employed (Panel C).
Figure 6:
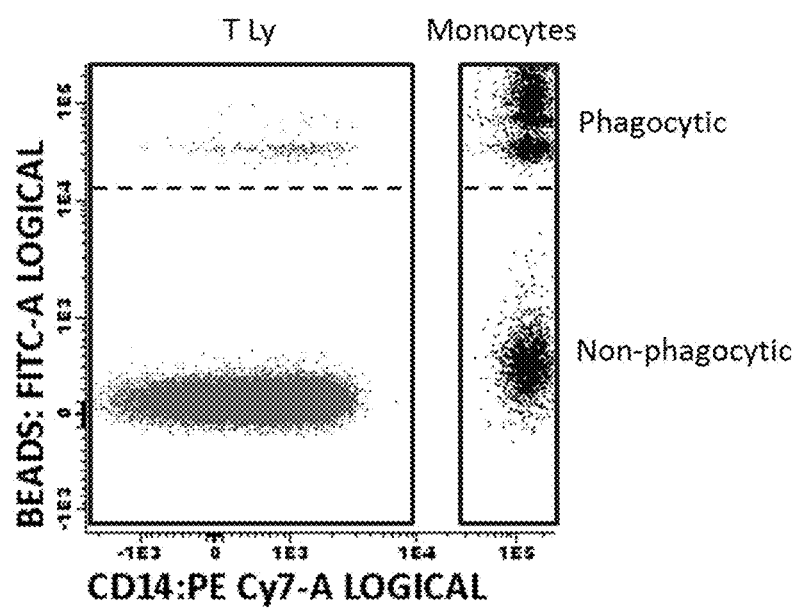
FIG. 6—Results of phagocytosis analysis after incubation of PBMN cells with carboxylate-modified polystyrene fluorescent yellow-green latex beads for 4 h at a ratio of 5 beads per cell. The fluorescence detected in the FITC channel (corresponding to the fluorescent yellow-green marker of the beads) allows the precise discrimination between phagocytic and non-phagocytic cells. In an FITC-CD14 dot plot is possible to recognize with high accuracy those phagocytic monocytes (CD14$^+$/FITC$^+$) from those non-phagocytic ones (CD14$^+$/FITC$^-$). The same strategy is performed for phagocytic and non-phagocytic T lymphocytes (CD14$^-$/FITC$^+$ and CD14$^-$/FITC$^-$, respectively).

Data analysis was performed in five steps. First, we selected the cells of interest (white blood cells) and excluded cell debris and cell aggregates, based on the expression of CD45 and light dispersion characteristics (forwards side scatter—FSC—and sideward side scatter—SSC—). Secondly, we identified and selected the monocytes ($CD14^{++}/CD4^+/CD3^-/CD45^+$), the T-CD4+ lymphocytes ($CD45^{++}/CD3^+/CD4^+/CD14^-$), and the T-CD4− lymphocytes ($CD45^{++}/CD3^+/CD4^-/CD14^-$) (FIG. 3). Thirdly, we selected Annexin V-CF™Blue positive cells within each population corresponding to apoptotic cells (FIG. 4). Afterwards, non-annexin positive cells (corresponding to viable cells) were used for determining TNFalpha-APC positive cells (for measuring the immune response) (FIG. 5). The effect of the stimulation in each cell population was assessed on unstimulated samples as a control and TNFalpha production was based on the percentage of positive cells, after subtracting the percentage of cells staining above the threshold for positivity in the negative control. Finally, phagocytic cells were identified selecting positive cells in the FITC channel (FIG. 6).

2.4. Results

PBMN cells incubation with carboxylate-modified polystyrene 2 μm fluorescent yellow-green latex beads did not induce apoptosis in any of the T cell populations analyzed (less than 1% apoptosis induction compared to a control without beads) at both 5 and 10 beads/cell ratio. Conversely, slight induction of apoptosis was detected on monocytes (18.7±3.2% and 21.8±0.3% Annexin $V^+$ cells with a ratio of 5 and 10 beads/cell, respectively, vs. 13.1±3.7% in the control without beads).

Similarly, incubation with latex beads did not lead to activation of either monocytes or T cells (less than 5% TNFalpha$^+$ cells vs. baseline activation detected in the control condition without beads) at both ratios tested.

Phagocytosis of latex beads was significantly observed on monocytes, with higher phagocytosis levels for conditions incubated at a ratio of 10 beads/cell compared to 5 beads/cell (72.4±2.0% vs. 48.7±0.7%, respectively).

2.5 Conclusion

According to these results, this novel approach allows in one single step the simultaneous multiparametric and quantitative analysis of phagocytosis, viability and immune response against dye-labeled beads.

Example 3—Assessment of Phagocytosis Using Non-Fluorescent Microparticles 3.1. Material and Methods Peripheral blood (PB) was obtained by venous puncture from 2 healthy individuals, placed in liquid lithium heparin tube and processed within the first 2 hours after collection for simultaneous analysis of viability, phagocytosis and immune response to incubation with microcapsules.

3.2. Sample Preparation

Peripheral blood mononuclear cells (PBMN cells) were purified by density gradient centrifugation using Biocoll Separating Solution (Biochrom, Germany), according to the manufacturer's protocol. After centrifugation, the PBMN cell interphase was collected and quantified using a Neubauer chamber.

A total of $0.2 \times 10^6$ PBMCs were cultured in RPMI-1640 medium supplemented with 10% heat-inactivated fetal bovine serum, 1% glutamine, 1% penicillin/streptomycin and 40 μM TACE inhibitor—TAPI-2—(Sigma-Aldrich, St. Louis/MO, USA) in a 24-well plate (2 cm$^2$ diameter). TAPI-2 was used as secretion blocking agent to reveal the levels of TNFalpha. The sample was incubated with $1 \times 10^6$ and $2 \times 10^6$ non-fluorescent beads (2 μm diameter) for 5 beads/cell and 10 beads/cell conditions, respectively. The wells were incubated in darkness at 3° C. in 5% CO$_2$ atmosphere for 4 hours.

After this incubation period, cells from each well were collected in a tube using phosphate buffer saline solution (PBS). If necessary, a cell scraper was used to detach the adherent cells. Then, cells were centrifuged at 400 g for 10 minutes. The supernatant was discarded and the cell pellet was resuspended in 2 mL of PBS. Another centrifugation (400 g, 10 minutes) was performed and cells were finally resuspended in 0.1 mL of PBS solution.

Afterwards, each sample was incubated with five monoclonal antibodies. The specificity of the monoclonal antibodies used, their origins and their fluorochromes were as follows:

CD3 APC-H7 (Clone SK7); T-lymphocyte marker (BD, San Jose/Calif., USA)

CD4 PE (Clone HP2/6); cytotoxic T-lymphocyte marker (ImmunoStep, Salamanca)

CD14 PE-Cy7 (Clone RM052); monocyte marker (BD, San Jose/Calif., USA)

CD45 PerCPCy5.5 (Clones 2D1); pan-leucocyte marker (BD, San Jose/Calif., USA)

TNFalpha APC (Clone MAb11); immune response marker (BD, San Jose/Calif., USA)

The tubes were gently vortexed and incubated in the dark for 15 minutes at room temperature. Immediately after this incubation period, 2 mL of PBS was added to each tube followed by gentle vortex. Then, samples were centrifuged at 400 g for 5 minutes. The supernatant was discarded and a new centrifugation step was performed. Afterwards, 0.2 mL of 1× annexin V binding buffer was added followed by the annexin V-CF™Blue apoptosis marker (ImmunoStep, Salamanca/Spain). Cells were incubated for 15 minutes at room temperature and were stored at 4° C. in the darkness until analyzed in the flow cytometer.

3.3. Data Acquisition and Analysis

Data acquisition was performed on a FACSCanto II flow cytometer (Becton Dickinson Biosciences, BD, San Jose/Calif., USA) using the FACSDiva software (v6.1; BD). For data analysis, the Infinicyt™ software (Cytognos SL, Salamanca, Spain) was used.

Figure 7:
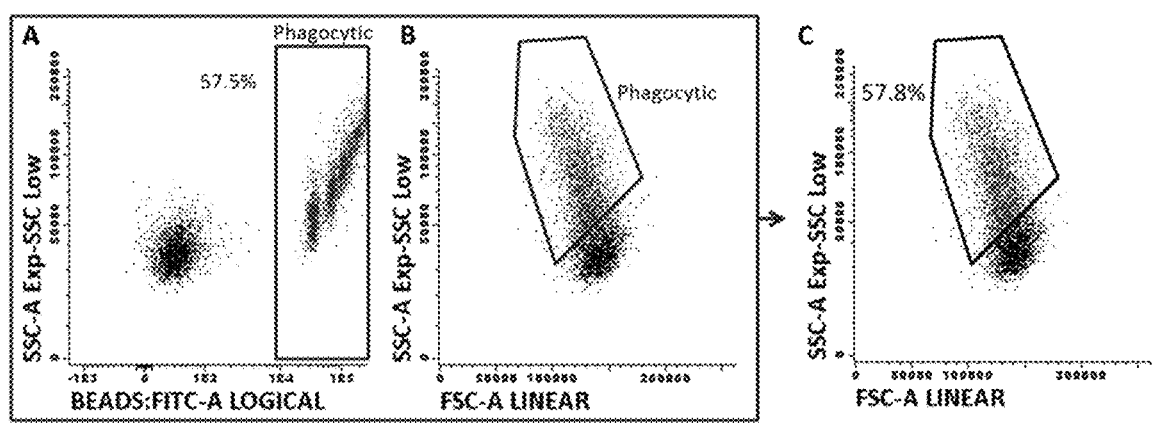
FIG. 7—Strategy of analysis of phagocytosis for non-fluorescent microparticles. In the left, two dot plots showing the gating of phagocytic cells by two different but comparable strategies. Detection of positive cells in the FITC channel (Panel A) corresponding to cells phagocyting fluorescent yellow-green beads. In Panel B, gating of cells with high SSC corresponding to the same cells gated in Panel A. Therefore, for non-fluorescent beads, the FSC-SSC dot plot (Panel C) can be used for identifying the phagocytic cells by using the threshold set for fluorescent beads (Panel B).

Data analysis was performed in five steps. First, we selected the cells of interest (white blood cells) and excluded cell debris and cell aggregates, based on the expression of CD45 and light dispersion characteristics (forwards side scatter—FSC—and sideward side scatter—SSC—). Secondly, we identified and selected the monocytes (CD14$^{++}$/CD4$^+$/CD3$^-$/CD45$^+$), the T-CD4$^+$ lymphocytes (CD45$^{++}$/CD3$^+$/CD4$^+$/CD14$^-$), and the T-CD4$^-$ lymphocytes (CD45$^{++}$/CD3$^+$/CD4$^-$/CD14$^-$) (FIG. 3). Thirdly, we selected Annexin V-CF™Blue positive cells within each population corresponding to apoptotic cells (FIG. 4). Afterwards, non-annexin positive cells (corresponding to living cells) were used for determining TNFalpha-APC positive cells (for measuring the immune response) (FIG. 5). The effect of the stimulation in each cell population was assessed on unstimulated samples as a control and TNFalpha production was based on the percentage of positive cells, after subtracting the percentage of cells staining above the threshold for positivity in the negative control. Finally, phagocytic cells were identified by comparing the SSC/FSC plot obtained with size-matched fluorescent-beads (Example 2). After selecting phagocytic cells as FITC positive cells (for fluorescent beads), SSC/FSC plot was employed as a template for phagocytic cells of non-fluorescent beads (FIG. 7).

3.4 Results

Analysis strategy for phagocytosis assessment of fluorescent beads was performed in the same samples using the methodology for analysis of phagocytosis of non-fluorescent beads. Overall, a significant correlation was observed between the two methods of analysis ($R^2$=0.934; p<0.01), as similar results were obtained for both the 5 beads/cell (57.0±0.8% phagocytosis using the method for fluorescent beads vs. 52.5±4.5% phagocytosis using the method for non-fluorescent beads) and 10 beads/cell (77.3±2.8% phagocytosis using the method for fluorescent beads vs. 75.6±2.6% phagocytosis using the method for non-fluorescent beads) conditions.

The invention claimed is:

1. A method for simultaneous evaluation of cytotoxicity, immune modulation and phagocytosis induction of a fluorescently-labeled material, said material being a natural, incidental or manufactured material containing particles, in an unbound state or as an aggregate or as an agglomerate and where one or more of its external dimensions comprises a size ranging from 0.001 µm to 1000 µm, comprising the following steps:
   a) incubating a biological sample with the fluorescently-labeled material, giving rise to stimulated cell populations;
   b) incubating the stimulated cell populations from the biological sample of step a) with the following molecules
      fluorochrome-labeled antibodies specific for monocytic markers, T-CD4$^+$ lymphoid markers, T-CD4$^-$ lymphocyte-associated markers and markers of molecules involved in immune modulation,
      an inhibitor of protein secretion, and
      viability cell markers,
      wherein each marker and the fluorescently-labeled material is detected with a different fluorochrome,
   c) passing the cell populations resulting from carrying out step b) through a flow cytometer and measuring the different fluorescent emissions in a single measurement; and
   d) counting the number of viable cells, activated cells and cells that have phagocytosed the fluorescently-labeled material within each cell population by measuring the amount of fluorescent signal associated with every individual cell and to every individual immune modulation involved molecule marker, viability marker and phagocytosed particle marker used.

2. The method according to claim 1, wherein the fluorescently-labeled material is a nanomaterial or a micromaterial.

3. The method according to claim 1, wherein the biological sample is selected from the group consisting of peripheral blood, ascitic fluid, pleural effusion, cerebrospinal fluid, bone marrow, lymph node, lymph fluid, synovial fluid, a single cell suspension prepared from a solid tissue and cell lines.

4. The method according to claim 1, wherein the monocytes, T-CD4$^+$ lymphocytes and T-CD4$^-$ lymphocytes markers are selected from the group consisting of CD14, CD4, CD3, CD45 and any combination thereof.

5. The method according to claim 1, wherein the viability cell markers are selected from the group consisting of Annexin V, Propidium Iodide (PI); 4′,6-Diamidino-2-phenylindole dihydrochloride (DAPI); 7-amino-actinomycin D (7-AAD); TO-PRO-3 and DNA-binding dyes.

6. The method according to claim 1, wherein the markers of molecules involved in immune modulation are selected from the group consisting of Tumor Necrosis Factor alpha (TNFalpha), Interferon gamma (IFNγ), Interleukin 6 (IL6), Interleukin 12 (IL12), Tumor Necrosis Factor beta (TNFβ), Interleukin 2 (IL2), Interleukin 8 (IL8), Interleukin 10 (IL10), Interleukin 13 (IL13), Interleukin 16 (IL16) and any combination thereof.

7. The method according to claim 1, wherein the fluorochromes are selected from the group consisting of fluorescein isothiocyanate (FITC), phycoerythrin (PE), peridinin chlorophyll protein (PerCP), allophycocyanin (APC), Alexa fluor 488, Alexa 647, Alexa 710, Alexa fluor 405, cyanin 5 (Cy5), Cyanin 5.5 (Cy5.5), pacific blue (PacB), horizon V450 (HV450), pacific orange (PacO), brilliant violet (BV), Horizon V500, 00515, Krome Orange, CF Blue, quantum dots or conjugates thereof coupled to PE, APC or PerCP, and any combination thereof.

8. The method according to claim 1, wherein the inhibitor of protein secretion is a metalloprotease inhibitor.

9. The method for analyzing the biocompatibility of a fluorescently-labeled material, said material being a natural, incidental or manufactured material containing particles, in an unbound state or as an aggregate or as an agglomerate and where one or more of its external dimensions comprises a size ranging from 0.001 µm to 1,000 µm, comprising:
   measuring the cytotoxicity, immune modulation and phagocytosis inducing properties of the fluorescently-labeled material by a method according to claim 1,
   wherein a lower degree of cytotoxicity, immune activity, and/or phagocytosis function than a control profile obtained by the same method but without the presence of the fluorescently-labeled material, is indicative that the fluorescently-labeled material is biocompatible.

10. The Method according to claim 9, wherein the fluorescently-labeled material is a nanomaterial or a micromaterial.

* * * * *